(12) United States Patent
Wehba et al.

(10) Patent No.: US 8,271,106 B2
(45) Date of Patent: Sep. 18, 2012

(54) SYSTEM AND METHOD FOR CONFIGURING A RULE SET FOR MEDICAL EVENT MANAGEMENT AND RESPONSES

(75) Inventors: Steven R. Wehba, Carlsbad, CA (US); Timothy L. Ruchti, Gurnee, IL (US)

(73) Assignee: Hospira, Inc., Lake Forest, IL (US)

(*) Notice: Subject to any disclaimer, the term of this patent is extended or adjusted under 35 U.S.C. 154(b) by 242 days.

(21) Appl. No.: 12/761,107

(22) Filed: Apr. 15, 2010

(65) Prior Publication Data

US 2010/0268157 A1 Oct. 21, 2010

Related U.S. Application Data

(60) Provisional application No. 61/170,205, filed on Apr. 17, 2009.

(51) Int. Cl.
*G06F 19/00* (2011.01)
(52) U.S. Cl. .............................. 700/89; 700/86; 704/257
(58) Field of Classification Search .................. 700/80, 700/86, 89; 704/257
See application file for complete search history.

(56) References Cited

U.S. PATENT DOCUMENTS

| | | | |
|---|---|---|---|
| 5,249,260 A * | 9/1993 | Nigawara et al. ............... 706/45 |
| 5,738,102 A | 4/1998 | Lemelson | |
| 6,669,630 B1 | 12/2003 | Joliat et al. | |
| 6,774,786 B1 | 8/2004 | Havekost et al. | |
| 6,775,577 B2 | 8/2004 | Crnkovich et al. | |
| 6,876,303 B2 | 4/2005 | Reeder et al. | |
| 7,079,035 B2 | 7/2006 | Bock et al. | |
| 7,099,809 B2 * | 8/2006 | Dori .................................. 703/6 |
| 7,117,041 B2 | 10/2006 | Engleson et al. | |
| 7,250,856 B2 | 7/2007 | Havekost et al. | |
| 7,289,948 B1 | 10/2007 | Mohri | |
| 7,315,825 B2 * | 1/2008 | Rosenfeld et al. ................. 705/2 |
| 7,319,386 B2 | 1/2008 | Collins, Jr. et al. | |
| 7,384,410 B2 | 6/2008 | Eggers et al. | |
| 2002/0169636 A1 * | 11/2002 | Eggers et al. ...................... 705/3 |
| 2003/0036683 A1 * | 2/2003 | Kehr et al. ..................... 600/300 |
| 2004/0077934 A1 | 4/2004 | Massad | |
| 2004/0236240 A1 | 11/2004 | Kraus et al. | |
| 2005/0020886 A1 | 1/2005 | Hutchinson et al. | |
| 2005/0246416 A1 * | 11/2005 | Blomquist ..................... 709/203 |
| 2006/0047538 A1 * | 3/2006 | Condurso et al. .................. 705/3 |
| 2007/0073419 A1 | 3/2007 | Sesay | |
| 2007/0106126 A1 | 5/2007 | Mannheimer et al. | |
| 2007/0169008 A1 | 7/2007 | Varanasi et al. | |
| 2007/0191973 A1 | 8/2007 | Holzbauer et al. | |
| 2007/0232867 A1 | 10/2007 | Hansmann | |
| 2007/0299389 A1 | 12/2007 | Halbert et al. | |
| 2010/0268157 A1 * | 10/2010 | Wehba et al. .................... 604/66 |

OTHER PUBLICATIONS

"Requirements for Medical Modeling Languages", Van Der Maas et al, Journal of the American Medical Informatics Association, vol. 8, No. 2, Mar./Apr. 2001.*

(Continued)

*Primary Examiner* — Michael D Masinick
(74) *Attorney, Agent, or Firm* — Michael R. Crabb

(57) ABSTRACT

A system and method to configure a rule set used in connection with a medical monitoring system for monitoring patients and patient care equipment, especially medication delivery pumps, based on a variety of conditions and parameters associated with monitored biometric information and equipment information and for providing user-defined responses to those conditions and parameters.

23 Claims, 5 Drawing Sheets

OTHER PUBLICATIONS

"A Regular Language: The Annotated Case Report Form", Wilkins et al, PPD Inc, 2011.*

"Augmented BNF for Syntax Specifications: ABNF", Network Working Group, Standards Track, Jan. 2008.*

* cited by examiner

SYSTEM AND METHOD FOR CONFIGURING A RULE SET FOR MEDICAL EVENT MANAGEMENT AND RESPONSES

CROSS-REFERENCE TO RELATED APPLICATIONS

This application claims priority under 35 U.S.C. 119 of U.S. Ser. No. 61/170,205 filed on Apr. 17, 2009.

FEDERALLY SPONSORED RESEARCH OR DEVELOPMENT

None.

TECHNICAL FIELD

The present invention relates to medical monitoring systems for monitoring hospital patients and patient care equipment based on a variety of parameters and conditions associated with monitored biometric or physiological information and equipment information and for providing user-defined responses to those parameters and conditions.

BACKGROUND AND SUMMARY OF THE INVENTION

Modern medical care often involves the use of medication management systems, which include medication delivery and monitoring devices such as medication delivery pumps and/or patient parameter monitors. Medication management systems for configuring, controlling, and monitoring medication delivery devices have been disclosed. For example, commonly owned U.S. patent application Ser. No. 10/930,358, which published as US20050144043A1 on Jun. 30, 2005 and U.S. patent application Ser. No. 10/783,573, which published as US20050278194A1 on Dec. 15, 2005, disclose a medication management system wherein customizable drug library or medical device configuration information is prepared using a drug library editor (DLE) program and module of a medication management unit (MMU). The MMU downloads the customizable drug library to the medication delivery pump and receives status or activity information from the pump. Commonly owned U.S. patent application Ser. No. 10/783,877, which published as WO2005050526A2 on Jun. 2, 2005, discloses how the drug library or medical device configuration information is created, edited, stored and communicated to a medication delivery device in the context of a medication management system to deliver substances, such as fluids and/or fluid medication to patients.

According to the above-mentioned commonly owned published patent applications, a typical medication management system includes a point of care computer, such as a barcode point of care computer and/or pharmacy computer, and/or an MMU, in communication with one or more medication delivery devices. The point of care computer(s) and/or the MMU, with associated memory, store various information, such as patient information, prescription information, customized drug library or other information, for managing medication delivery to a patients, such as performing five-rights checking, configuring the medication delivery devices, and receiving and storing activity information received from the medication delivery devices.

Caregivers use outputs from patient monitoring and equipment monitoring devices to make various patient care decisions. Patient monitoring devices and patient care equipment monitoring devices may be connected to a receiver, which receives the output signals from the patient monitoring devices and patient care equipment monitoring devices. In some cases, the receivers may display and/or record the information from the patient and patient care equipment monitoring devices. In other cases, the devices may include a monitor and/or recording medium. The receivers or devices may also have preset or adjustable alarms that are triggered when one of the outputs from the patient or patient care equipment monitoring devices deviates from a pre-set limit.

One drawback of such conventional monitoring systems is the occurrence of false positive alarms. Such false positive alarms may occur due to a momentary deviation of a monitored state that deviates from the pre-set limits, but which rapidly returns to a normal state. For example, one application of such a conventional alarm monitoring system is for use in monitoring a patient's reaction to a controlled administration of analgesia. In such systems, currently practiced technologies are subject to the following problems: (1) false alarms due to erroneous respiratory or blood gas readings associated with motion artifacts or poor sensor placement and coupling; and (2) false alarms resulting from patient circumstances in which monitored conditions are not truly indicative of an adverse event. Such an alarm may be triggered, for example, if a patient monitor is briefly disconnected from a monitoring device. False positive alarms waste the time of hospital personnel who need to respond to such alarms. Frequent false positive alarms may also desensitize medical responders to the alarm. In addition, a false positive alarm may cause a medial responder to take improper action believing that the alarm is a true alarm.

Another drawback of such conventional systems is the relative lack of ability to require a response only when there has been a change in multiple monitored parameters, such as a change in blood oxygen levels coupled with a change in breathing. Specifically, for monitoring analgesic application via a pump, alarms are typically associated with univariate parameters, such as $SpO_2$ alone or end tidal $CO_2$ ($ETCO_2$) alone, for detecting changes in these parameters consistent with respiratory depression. These systems are subject to a variety of problems due to the complexity of the body's response to analgesia and the insufficiency of a single variable to represent the range of clinical circumstances and patient parameters that may result from the administration. For example, an undesirable adverse event associated with administration of analgesics, sedatives and anesthetics can be depression of the patient's respiratory and/or central nervous systems. Exacerbating the risk to patients is the profound variation in drug efficacy between patients and through time. Consequently, avoidance of drug overdose is of particular concern to healthcare professionals and can result in the under administration of narcotics. The latter problem leads to unnecessary and significant discomfort and is associated with longer hospital stays and recovery times.

Yet another drawback of such systems is the difficulty of creating a readily customized rule set for monitoring, alarming and requiring responses thereto. Additionally, these systems typically lacked the ability to automatically respond to changes in a plurality of monitored conditions. Furthermore, such traditional systems often lacked the ability to automatically change from a first rule set to a second rule set based on a change in the monitored parameters.

The system disclosed herein is designed to enable hospital personnel to configure a rule set by inputting, via a user-interface, a wide variety of monitored patient or equipment parameters, and conditions associated with those parameters, which, when satisfied by inputs from the medical equipment and patient monitoring devices, trigger a user-defined or user-selected response. The rule set can include Boolean combinations of these parameters and respective conditions to establish a set of multi-variable inputs that must occur before a response is triggered. Authorized hospital personnel can also customize the type of parameter, the conditions for that parameter to be met and type of response for each rule set. The software utilized to implement this invention may use a context free grammar, specifically, Backus-Naur form metasyntax, to build the rule sets comprised of parameters, conditions and responses.

All of the patents and patent application referred to within this Background of the Invention section of the present specification are hereby incorporated by reference and made a part of this specification. In addition, the present invention is provided to solve the problems discussed above and, to provide advantages and aspects not provided by medical systems, as well as achieve other objects not explicitly stated above. A full discussion of the features, advantages and objects of the present invention is deferred to the following detailed description, which proceeds with reference to the accompanying drawings.

Other features and advantages of the invention will be apparent from the following specification taken in conjunction with the following drawings.

BRIEF DESCRIPTION OF THE DRAWINGS

To understand the present invention, it will now be described by way of example, with reference to the accompanying drawings in which.

DETAILED DESCRIPTION OF THE INVENTION

Figure 1:
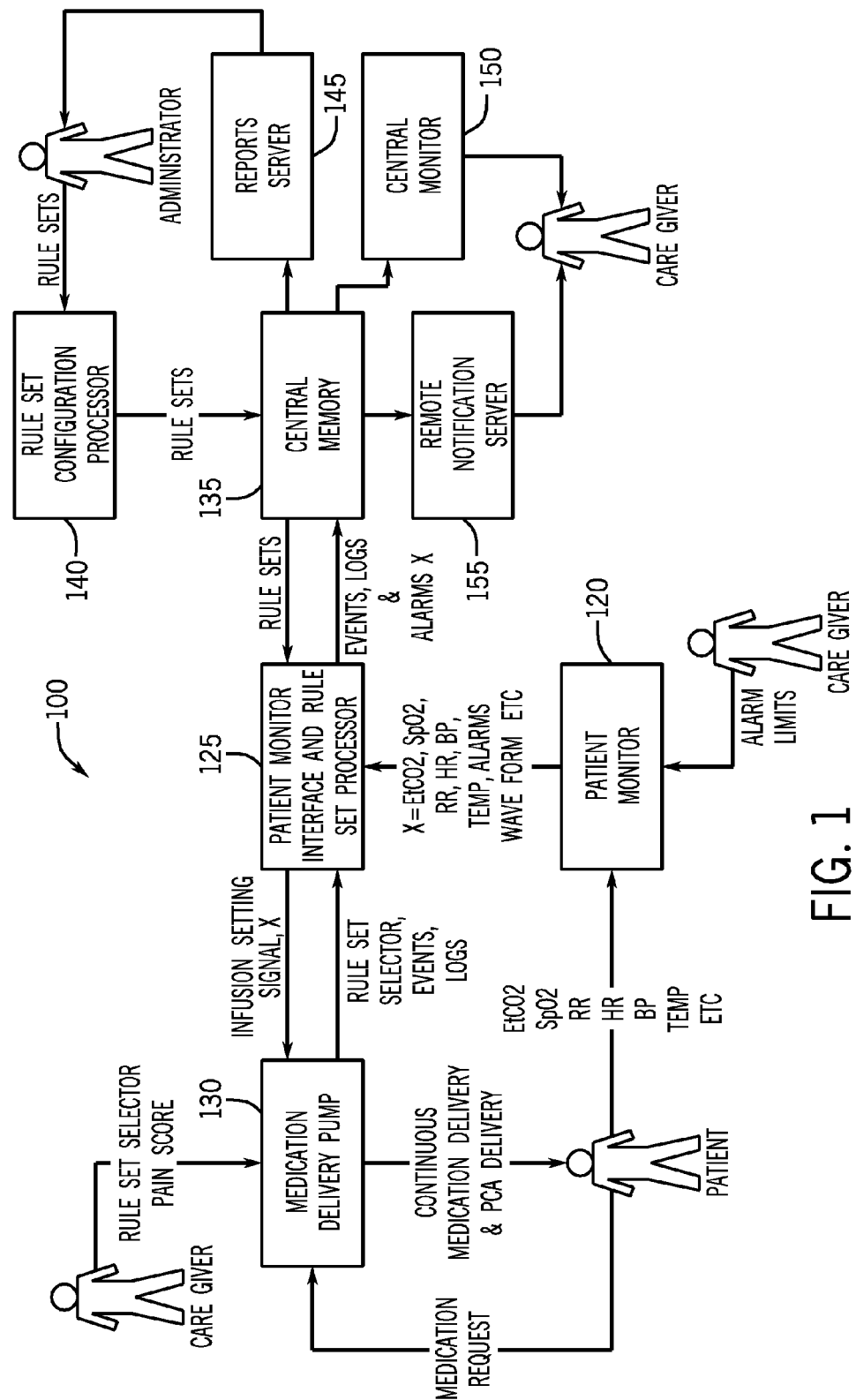
FIG. 1 is a diagram of one embodiment of a medication delivery device and patient monitoring system of the present invention.

While this invention is susceptible of embodiments in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated.

FIG. 1 shows an exemplary medical monitoring system for monitoring hospital patients and patient care equipment. As shown in FIG. 1, a medication management system 100 includes a patient monitor 120 for monitoring patient biometric or physiological information of various types. For example, the monitored information can include, but is not limited to, $ETCO_2$, $SpO_2$, respiratory rate, heart rate, blood pressure, temperature and other patient biometric, physiological or medical parameter information. The patient monitor may include appropriate biometric sensors for sensing the desired patient information, as known in the art. Such biometric sensors may include an EKG system, respiratory monitors, blood gas monitors, glucose monitors, blood analyte monitors and/or other measurement systems which monitor a physiological variables or analytes associated with a patient. For example, in the case of a system for patient controlled analgesia (PCA), a NELLCOR or MASSIMO monitor with an ORIDION capnography respiratory monitor board can be used to generate data, waveforms, and alarms associated with heart rates, $SpO_2$ levels, respiratory rates and $ETCO_2$ levels.

The patient monitor 120 can optionally include a processor and patient monitoring application for monitoring the information received by the various biometric sensors. Patient monitor 120 may include a user interface associated therewith to receive input from a patient or caregiver. A patient monitor processor compares the information received from the sensors and generates an alarm signal based on the comparison. Alarm signals can be generated if an alarm limit is met, or alternately when the alarm limit is exceeded. Alarm limits can include an upper limit, a lower limit, or both upper and lower limits that together define one or more acceptable ranges. Patient monitor 120 is communicatively networked with a patient monitor interface and rule set processor 125 for transmitting the monitored information and/or alarms to the patient monitor interface and rule set processor 125.

As shown in FIG. 1, a patient care device, which is shown as a medication delivery pump 130, may be operatively connected to or in communication with the patient. The medication delivery pump 130 may be configured for controlled delivery of a medication to the patient. The medical pump can be used with PCA (patient controlled analgesia) request devices in which a patient can "self-deliver" medication, such as an analgesia or analgesic. For example, U.S. Pat. No. 4,551,133, to Zeggers de Beyl et al., issued Nov. 5, 1985, and incorporated in its entirety herein by reference, discloses a patient controlled analgesia system for introducing medication to a peripheral vein of a patient. The delivery of the analgesic is controlled by a microprocessor based system in response to the patient's requests. Specifically, the microprocessor is associated with a remote patient control or PCA request device, for providing an actuation signal to the microprocessor when the patient requests a delivery of medication.

The system 100 may further have a plurality of medication delivery pumps 130 for the administration of a plurality of medications. The medication delivery pump may further include a user interface that permits a caregiver to provide inputs to the medication delivery pump 130. Such inputs may include a pain score associated with the patient, which may be used to determine the amount and frequency of patient controlled analgesic (PCA) permitted. In one embodiment, the medication delivery pump has a user interface configured to permit a caregiver to select a rule set, herein sometimes referred to as an algorithm, for monitoring the patient and patient care equipment and responding to inputs from the patient and patient care equipment, as described in greater detail below. In addition, the user interface on the medication delivery pump 130 provides a means, such as a push button or a touch screen interface, for a caregiver to respond to an alarm or an infusion event (for example, an infusion pause).

The medication delivery pump 130 is in communication with the patient monitor interface and rule set processor 125 for communicating information between the medication delivery pump 130, the patient monitor interface and rule set processor 125, the patient monitor 120, and other components of the system 100 as described below. As a result, medical pump information can be communicated from the medication delivery pump 130 to other components of the system 100. Such medical pump information may include both medical pump status information and medical event information. Medical pump status information can include but is not limited to whether an active delivery of medication is taking place, the rate of the delivery, volume (delivered or remaining to be delivered) and the length of time passed since the delivery began. Medical pump event information can include but is not limited to whether any alarms or alerts have issued since the last communication, whether an occlusion has taken place, and whether power was lost to the medical pump, among other medical pump event information. Status information and/or medication delivery status information is used herein to refer to at least medical pump status information, medical pump event information, and/or other status and/or event information. The medical delivery status information may be transmitted as historical logs of information or real time communication or information.

The medication delivery pump 130 may also communicate the rule set selected by a caregiver at the medication delivery pump 130 to the patient monitor interface and rule set processor 125. The patient monitor interface and rule set processor 125 is communicatively connected with a central memory 135, which has a library of rule sets or portions thereof stored therein. The library of rule sets can be a part of a customizable drug library or other libraries that can be downloaded to medical devices. In one embodiment, the patient interface and rule set processor 125 applies the selected rule set to the information received from the patient monitor 120, such as $ETCO_2$, $SpO_2$, respiratory rate, heart rate, blood pressure, temperature and other patient parameter information, and/or the information received from the medication delivery pump 130, such as the medical delivery status information, to the rule set. Depending upon whether the conditions and parameters of the rule set are satisfied, the patient interface and rule set processor 125 may generate an output signal to the medication delivery pump 130 that instructs the medication delivery pump to adjust the medication delivery in some manner.

In another embodiment, the patient monitor interface and rule set processor 125 may send information from the patient monitor 120 to the medication delivery pump 130 without processing it through a rule set. The medication delivery pump 130 or the patient monitor 120 may be configured to receive alarm limits inputted by a caregiver. The alarm limits may correspond to the patient information received at the medication delivery pump 130. Alternatively, or additionally, the alarm limits may relate to information regarding the medication delivery pump 130 itself. A pump processor compares the selected alarm limits to the relevant information, and, if the information satisfies (meets, exceeds, falls under or between) the alarm limits, generates an alarm signal from the pump 130. The alarm signal from the pump may be conveyed to the patient monitor and rule set processor 125 and to other components of the system 100 as described below.

The medication delivery pump 130 may display the patient information on a display screen of the medication delivery pump. The display screen may also display a variety of medical pump status information including but not limited to a patient identifier, room number, delivery mode, delivery rate, whether an active delivery of medication is taking place, how long since the delivery began, basal rate, PCA bolus amount, lockout period for the PCA bolus, and lockout volume for the PCA bolus.

In an alternative embodiment that will be easily understood by one skilled in the art in view of the figures and description herein, the patient monitor interface and rule set processor 125 could be a part of either the medication delivery pump 130 or the patient monitor 120 or another component of the system rather than a separate unit. Processing capacity and functions can be distributed among the components of the system 100 as shown and described or they can be rearranged and/or combined within any of the other processors in the system.

The central memory 135 is in communication with a rule set configuration processor 140. The rule set configuration processor 140, which may be a personal computer, personal digital assistant (PDA) or the like, has a user input that permits an administrator to create and configure a rule set, sometimes referred to herein as an algorithm, as described in greater detail below. The rule set is then sent to and stored in the central memory 135.

The central memory 135 also may receive certain information from the patient monitor interface and rule set processor 125. Specifically, the central memory 135 may receive logs of the patient information generated by the patient monitor 120 and the medication delivery pump information generated by the medication delivery pump 130. This information may also be sent to the central memory 135 from the patient monitor interface and rule set processor 125 in real time.

The central memory 135 may also store information related to the patient's medical history and recent medical treatments, and, in particular, the patient's recent history of infused medication. This information may be accessed by the patient monitor interface and rule set processor 125 or any other component of the system 100 when such information is required as an input for processing a rule set. For example, a rule set may require inputs regarding the amount of a drug still active in the patient, which could be determined based on the amount of the drug that the patient has received and how recently the drug was delivered to the patient, which would be stored in the central memory 135. A detailed example of such a rule set is described below.

The central memory 135 may also receive outputs from the patient monitor interface and rule set processor 125 that are generated as a response to processing inputs via a rule set. Specifically, if the parameters and associated conditions of a certain rule set are satisfied, the patient monitor interface and rule set processor 125 may send an alarm instruction to the central memory 135, which may then be sent to a caregiver, as described below. In another example, if the parameters and conditions of a rule set are satisfied, the patient monitor interface and rule set processor 125 may send a signal to the central memory 135 to access a different rule set stored in the central memory 135.

The central memory 135 may further distribute the information that it receives from the patient monitor interface and rule set processor 125 to a reports server 145, a central monitor 150 and a remote notification server 155. In particular, the reports server 145 may receive summaries, overviews and logs of the medication delivery pump information and the patient monitor information for generating reports that can be sent to or made available to administrators. The central monitor 150 may receive similar information for displaying information from the medication delivery pump 130 and patient monitor 120 and provide this information to a caregiver at a location remote from the patient. The remote notification server 155 will typically receive instructions to notify caregivers of certain changes in patient or equipment status. For example, if the parameters and conditions of a rule set are satisfied and the rule set dictates that a caregiver should be notified in such an event, the remote notification server 155 will generate a notification to the caregiver. Such notifications may be conveyed to one or more small personal digital assistant computers including but not limited to a pager, cell phone or PDA that is in communication with the remote notification server 155. The small digital assistant computers can be carried by the caregivers and used by them to identify themselves through the use of built in barcode scanners or otherwise as they perform certain caregiving functions, such as performing scheduled rounds in which the caregivers deliver medication to patients in patient rooms within a caregiving facility.

In an alternative embodiment, the reports server 145, central monitor 150 and remote notification server 155, or any combination of these devices may be networked directly to the patient monitor interface and rule set processor 125, the pump 130 and/or the patient monitor 120.

Communication of information between the various components of the system may occur in a variety of ways. Information may be communicated between the various devices in a real-time constant stream, the information may be pushed from the sending to device to the receiving device on a periodic basis or on a continuous loop, the information may be pulled from the sending device by the receiving device on a periodic basis or on a continuous loop, and/or the various devices may be configured to push or pull the information based on various triggering events, for example, the passage of time or once a certain amount of information has been accumulated. The components of the system shown in FIG. 1 are described in greater detail below.

The medication delivery pump or medical pump 130 includes but is not limited to enteral pumps, infusion pumps, cassette pumps, syringe pumps, peristaltic pumps, or any fluid pumping device for the delivery of fluids intravenously, intra-arterially or otherwise to a patient. A pump processing unit or pump processor may be included in pump 130 and performs various operations, as described in greater detail herein. An input/output device or user interface communicates with the pump processing unit and allows the user to receive output from pump processing unit and/or input information or commands into the pump processing unit. Those of ordinary skill in the art will appreciate that input/output device may be provided as a separate display device and/or a separate input device. For example, in one embodiment of the present invention, the medical pump 130 includes a patient-controlled analgesia (PCA) request device which is in electrical communication with the processor, for receiving an input from a person to generate a medication request signal from the PCA request device.

A pump memory communicates with the pump processor and stores code and data necessary for the pump processor to calculate and output the operating parameters of the pump 130. The pump memory stores a programming code, such as a medication delivery programming code or application for processing data to determine and control the operating parameters of the medical pump 130.

With continued reference to FIG. 1, the medical pump 130 can also include a communications engine or interface, in electrical communication with the pump processor, for transmitting/receiving communications between the pump processor, the patient parameter monitor 120, and the patient monitor interface and rule set processor 125, as described in detail herein. In fact, in one embodiment where the rule set processing function is integrated into the pump 130, the communication engine also serves as the patient monitor interface.

The central memory 135 can include a central programming code, such as a central medication management application and/or central patient monitoring application and other applications, for execution by the central processor, which can perform various medication management, patient monitoring, and other functions, as described in greater detail herein. Further, the medical pump 130 can include many aspects of a LifeCare PCA® Infusion System, and the medication management application within the central memory 135 can include many aspects of Hospira MedNet® Software, both manufactured and sold by Hospira, Inc., the assignee of the present invention, in conjunction with the present invention.

Generally, in terms of hardware architecture, as shown in FIG. 1, the medical pumps 130, patient parameter monitors 120, patient monitor interface and rule set processor 125, rule set configuration processor 140, central monitor 135, reports server 145, and remote notification server 155 of the medication management and/or patient parameter monitoring systems 100, may each include a processor, memory, and one or more input and/or output (I/O) devices (or peripherals) that are communicatively coupled via a local interface. The local interface can be, for example, but not limited to, one or more buses or other wired or wireless connections, as is known in the art. The local interface may have additional elements, such as cables, controllers, buffers (caches), drivers, repeaters, and receivers, to enable communications. Further, the local interface may include address, control, and/or data connections to enable appropriate communications among the other computer components.

The processors are hardware devices for executing software, particularly software stored in memory. The processors can be any custom made or commercially available processor, a central processing unit (CPU), an auxiliary processor among several processors associated with the medical pumps 130, patient parameter monitors 120, patient monitor interface and rule set processor 125, rule set configuration processor 140, central monitor 150, reports server 145 and remote notification server 155 of the medication management and/or patient parameter monitoring system 100, a semiconductor based microprocessor (in the form of a microchip or chip set), a macroprocessor, or generally any device for executing software instructions. Examples of suitable commercially available microprocessors are as follows: a PA-RISC series microprocessor from Hewlett-Packard Company, an 80×86 or Pentium series microprocessor from Intel Corporation, a PowerPC microprocessor from IBM, a Sparc microprocessor from Sun Microsystems, Inc., or a 68xxx series microprocessor from Motorola Corporation. The processors may also represent a distributed processing architecture such as, but not limited to, EJB, CORBA, and DCOM. In one embodiment, the central memory 135 and reports server 145 is on a WINDOWS based server or series of servers.

Each memory of each of the medical pumps 130, patient parameter monitors 120, patient monitor interface and rule set processor 125, rule set configuration processor 140, central monitor 150, reports server 145 and remote notification server 155 of the medication management and/or patient parameter monitoring systems 100, can include any one or a combination of volatile memory elements (e.g., random access memory (RAM, such as DRAM, SRAM, SDRAM, etc.)) and nonvolatile memory elements (e.g., ROM, hard drive, tape, CDROM, etc.). Moreover, these memories may incorporate electronic, magnetic, optical, and/or other types of storage media. The memories can have a distributed architecture where various components are situated remote from one another, but are still accessed by the processors of the medical pumps 130, patient parameter monitors 120, patient monitor interface and rule set processor 125, rule set configuration processor 140, central monitor 150, reports server 145, and remote notification server 155 of the medication management and/or patient parameter monitoring system 100.

The software within one or more of the above referenced memories may include one or more separate programs. The separate programs comprise ordered listings of executable instructions for implementing logical functions. In the examples of FIG. 1, the software in the memories can include suitable operating systems (O/S). A non-exhaustive list of examples of suitable commercially available operating systems for at least some of these devices is as follows: (a) a WINDOWS operating system available from Microsoft Corporation; (b) a NETWARE operating system available from Novell, Inc.; (c) a MACINTOSH operating system available from Apple Computer, Inc.; (d) a UNIX operating system, which is available for purchase from many vendors, such as the Hewlett-Packard Company, Sun Microsystems, Inc., and AT&T Corporation; (e) a LINUX operating system, which is freeware that is readily available on the Internet; or (f) a run time VXWORKS operating system from WindRiver Systems, Inc. The operating systems essentially control the execution of other computer programs, such as the medication delivery applications, network interface applications, patient monitoring applications, central medication management applications, central patient monitoring applications, and/or biometric applications, in accordance with the present invention, and provide scheduling, input-output control, file and data management, memory management, and communication control and related services.

The I/O devices referred to above may include input devices, for example input modules for PLCs, a keyboard, mouse, scanner, microphone, touch screens, interfaces for various medical devices, bar code readers, biometric receivers, PCA request devices, stylus, laser readers, radio-frequency device readers, etc. Furthermore, the I/O devices may also include output devices, for example but not limited to, output modules for PLCs, a printer, bar code printers, displays, etc. Finally, the I/O devices may further include devices that communicate both inputs and outputs, for instance but not limited to, a modulator/demodulator (modem; for accessing another device, system, or network), a radio frequency (RF) or other transceiver, a telephonic interface, a bridge, and a router.

Figure 2:
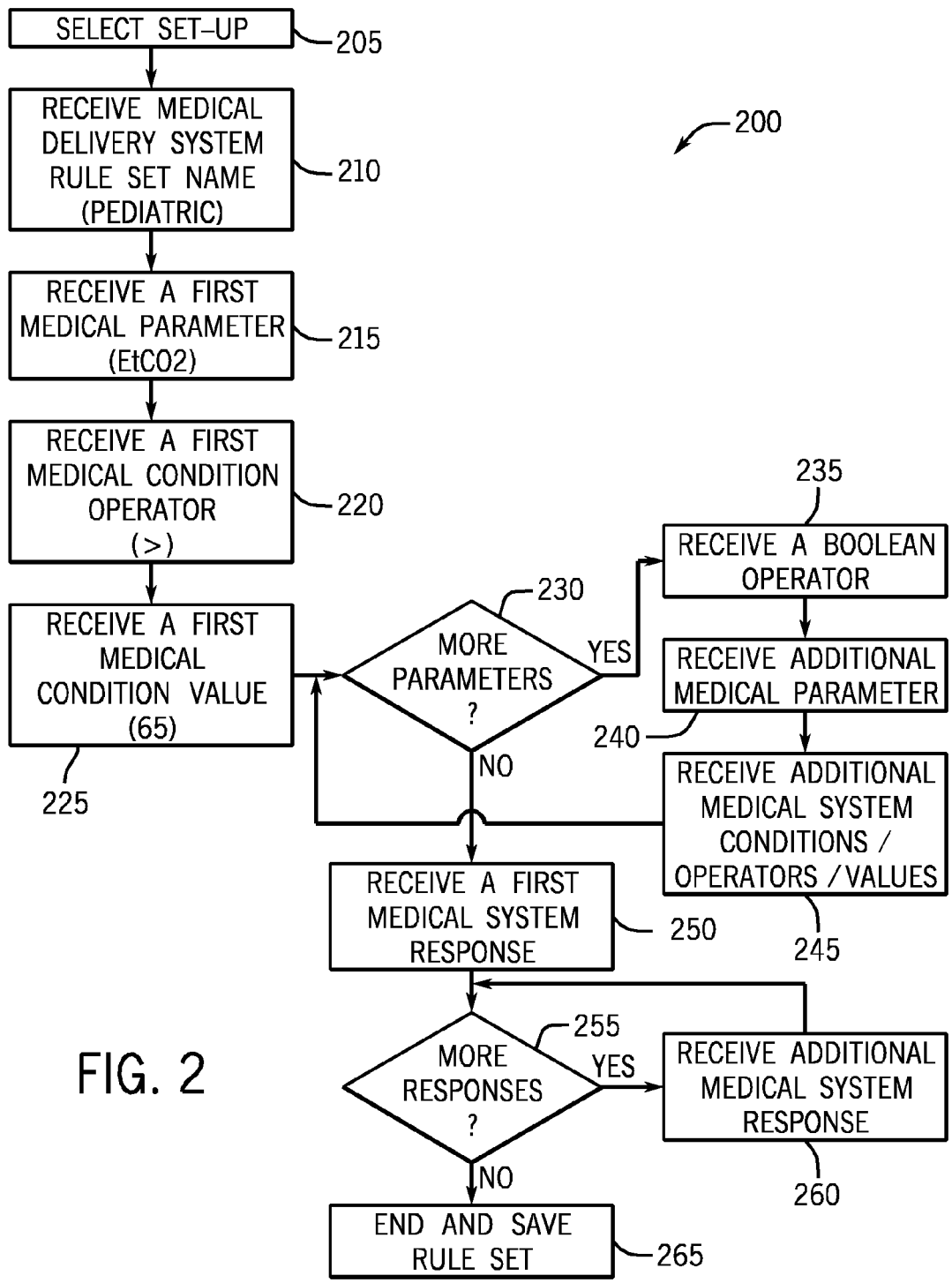
FIG. 2 is a flow chart of one embodiment of a system and method for configuring a rule set for use with a medication delivery device and patient monitoring system of the present invention.
Figure 3:
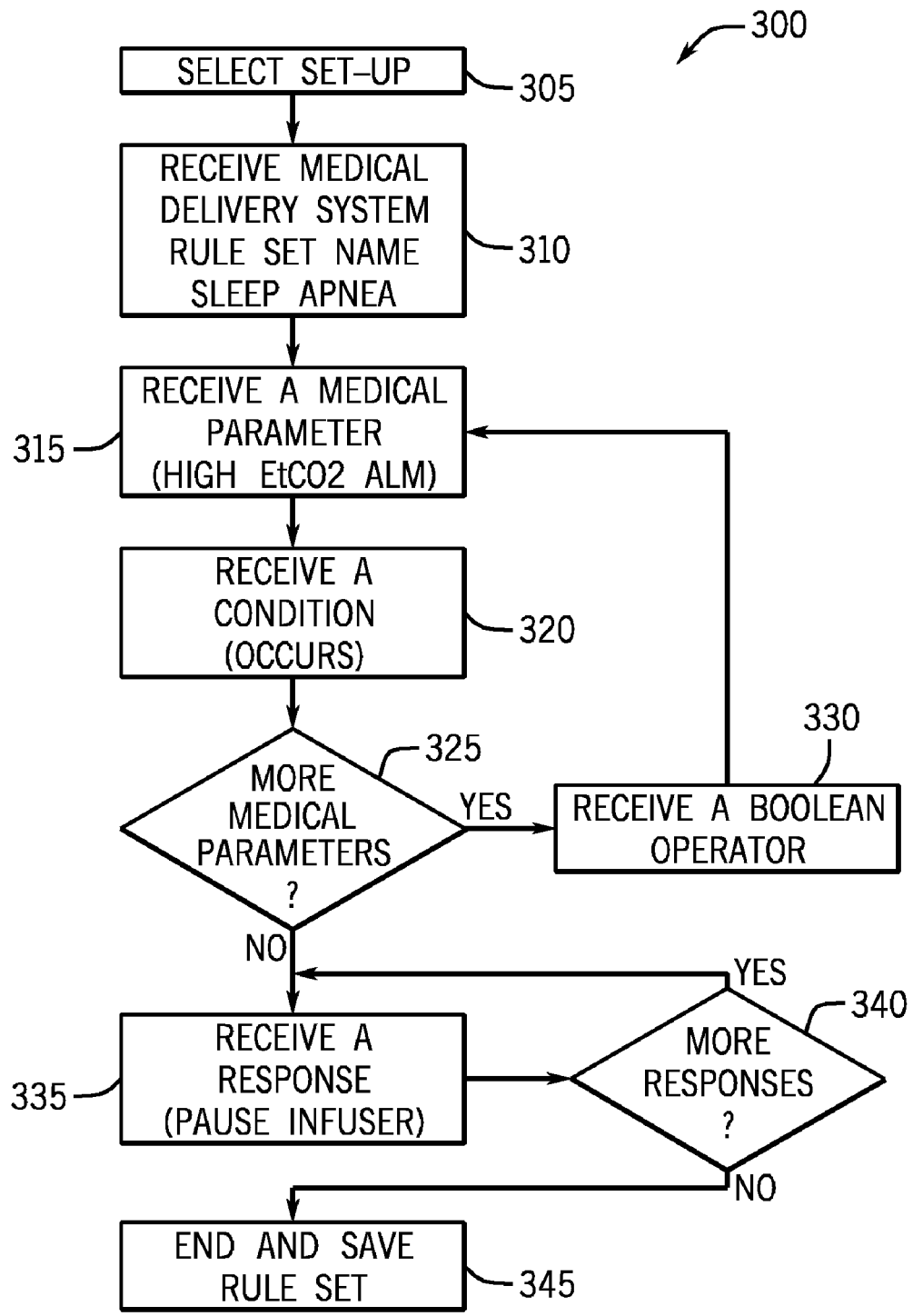
FIG. 3 is a flow chart of a second embodiment of a system and method for configuring a rule set for use with a medication delivery device and patient monitoring system of the present invention.

If the medical pumps 130, patient parameter monitors 120, patient monitor interface and rule set processor 125, rule set configuration processor 140, central monitor 150, reports server 145, and remote notification server 155 of the medication management and/or patient parameter monitoring system 100 are a PC, workstation, PDA, or the like, the software in the respective memories may further include a basic input output system (BIOS) (not shown in FIGS. 1, 2 and 3). The BIOS is a set of essential software routines that initialize and test hardware at startup, start the O/S, and support the transfer of data among the hardware devices. The BIOS is stored in ROM so that the BIOS can be executed when the medical pumps 130, patient parameter monitors 120, patient monitor interface and rule set processor 125, rule set configuration processor 140, central monitor 150, reports server 145, and remote notification server 155 of the medication management and/or patient parameter monitoring system 100 are activated.

When the medical pumps 120, patient parameter monitors 130, patient monitor interface and rule set processor 125, rule set configuration processor 140, central monitor 150, reports server 145, and remote notification server 155 of the medication management and/or patient parameter monitoring system 100, are in operation, the processors therein are configured to execute software stored within respective memories, to communicate data to and from memories, and to generally control operations of the components of the medication management and/or patient parameter monitoring system 100, pursuant to the software. The medication delivery applications, network interface applications, patient monitoring applications, central medication management applications, central patient monitoring applications, and/or biometric applications, and the O/S, in whole or in part, but typically the latter, are read by respective processors, perhaps buffered within the processors, and then executed.

When the medication management and/or patient parameter monitoring system 100 is implemented in software, as is shown in FIG. 1, it should be noted that the application programs therein can be stored on any computer readable medium for use by or in connection with any computer related system or method. In the context of this document, a computer readable medium is an electronic, magnetic, optical, or other physical device or means that can contain or store a computer program for use by or in connection with a computer related system or method. In the context of this document, a "computer-readable medium" can be any means that can store, communicate, propagate, or transport the program for use by or in connection with the instruction execution system, apparatus, or device. The computer readable medium can be for example, but not limited to, an electronic, magnetic, optical, electromagnetic, infrared, or semiconductor system, apparatus, device, or propagation medium. More specific examples (a non-exhaustive list) of the computer-readable medium would include the following: an electrical connection (electronic) having one or more wires, a portable computer diskette (magnetic), a random access memory (RAM) (electronic), a read-only memory (ROM) (electronic), an erasable programmable read-only memory (EPROM, EEPROM, or Flash memory) (electronic), an optical fiber (optical), and a portable compact disc read-only memory (CDROM) (optical). Note that the computer-readable medium could even be paper or another suitable medium upon which the program is printed, as the program can be electronically captured, via, for instance, optical scanning of the paper or other medium, then compiled, interpreted or otherwise processed in a suitable manner if necessary, and then stored in a computer memory.

As referenced above, an administrator, also referred to herein as an authorized user, may configure a rule set for use with the system 100 at a rule set configuration processor 140. A rule set includes one or more parameters, for example patient physiological or biometric parameters, which may have conditions associated with the respective parameters, and one or more responses.

Methods of creating, establishing, or receiving a rule set configuration 200 and 300 are shown in FIGS. 2 and 3, respectively and understood in view of FIG. 1. The rule set configuration processor 140 receives an instruction from the administrator to set up a new rule set at steps 205, 305. The rule set configuration processor 140 then receives a rule set name entered or selected by the user, for example "Pediatric" or "Sleep Apnea" at steps 210, 310. The rule set configuration processor 140 then receives a first medical system parameter entered by the user at steps 215, 315. The parameters may be associated with one of the types of information received by the patient monitor from the biometric sensors, such as the $ETCO_2$, $SpO_2$, respiratory rate or heart rate. The parameters may also relate to an alarm received from the patient monitor 120, for example, a "low blood pressure" alarm. The parameters could also relate to information received from the medication delivery pump 130 or an alarm from the medication delivery pump. After receipt of the medical parameter, a condition associated with that medical parameter and inputted by the authorized user is received. As shown at steps 220 and 225, where the parameter relates to a numerical value rather than a binary event, the condition may be comprised of a first medical condition operator, for example ">", "<", "=", or "≠" followed by a first medical condition value. As shown in FIG. 3 in step 320, when the medical parameter relates to a binary event, such as an alarm, after receipt of the medical parameter, the condition may be a simple binary state related to the parameter, such as "occurs" ("occurred") or "does not occur" ("has not occurred"). However, such conditions may, in some cases, have additional limitations, such as "occurs and persists for 30 seconds." Various possibilities come to mind in view of these examples in the context of the present specification.

As shown at steps 230, 325, the rule set configuration processor 140 is configured to optionally receive additional parameters, condition operators and/or condition values. If the administrator opts to enter additional parameters, conditions, and/or condition values, the administrator enters, and the rule set configuration processor 140 receives, a Boolean operator, for example including but not limited to AND, OR, NOT, etc. for connecting the multiple parameters, conditions, and/or condition values shown at steps 235, 330 and optionally additional parameters, conditions, and/or condition values as shown at steps 240, 245, 315, 320. As can be understood in view of FIGS. 3 and 4, one example of the second parameter/condition/value could be that a SpO$_2$ alarm occurs and persists for five minutes. One skilled in the art will recognize that this latter complex type of parameter/condition/ value state can itself be expressed or comprised of two separate, simpler states connected by a Boolean operator. For example, the first state can be expressed simply as a SpO$_2$ alarm occurs and the second state can be expressed as a SpO$_2$ alarm has persisted for more than five minutes. The two states can be connected by the Boolean operator AND. Alternatively, such complex states can be expressed through use of an optional decision block and loop through the conditions and/ or values within the parameter of interest. States can be expressed in a variety of ways including but not limited to that a condition occurs X times in Y seconds or for X of the last Y seconds. Other units of time such as minutes or hours could be selected by the user to configure the rule set.

Once all of the parameters have been received, the rule set configuration processor 140 is configured to receive a first medical system response, as shown at steps 250, 335, entered by the administrator. The medical system responses may include the generation of an update to a central monitoring system, generation of a prompt to a caregiver requiring input from the caregiver, or an automated adjustment of a patient care device. For example, one such response might be to send a message to the caregiver suggesting an alternate form of treatments. Another such response is to send a signal to the medication delivery pump instructing it to pause an infusion or modify the rate of infusion, for example by decreasing it. Yet another response can include a call to the central memory to retrieve a different, previously entered, rule set and to implement that different rule set. The call can be based on the name of the different rule set that has previously been created and stored, and therefore has a name to use to refer to it within the call process. As shown in steps 255, 260, and 335, 340, a user may enter a plurality of responses. Once all conditions and responses have been received by the rule set configuration processor 140, the configuration process is complete and the rule set is then saved at steps 265, 345.

Flexibility in permitting authorized users to configure rule sets that incorporate a variety of parameters, conditions and responses can be achieved by using a context free grammar such as a Backus Naur Format (BNF) code. A partial listing of an exemplary BNF code for building the rule sets is listed in Appendix A, hereto.

In the exemplary grammar in Appendix A, variables, which are referred to herein as non-terminal symbols are shown in angled brackets <and >. (It should be noted that use of the <conditions> symbol in the exemplary grammar in Appendix A is not intended to have the same meaning as the term "conditions" as used within other portions of the specification.) Each non-terminal symbol can be comprised of a number of alternatives. The alternatives for the non-terminal symbol are listed after the ::=sign and each alternative is separated by the | symbol. The alternatives may themselves be non-terminal symbols or they may be terminal symbols that are shown in quotes. The alternatives may also comprise both a non-terminal portion and a terminal portion. For the convenient reference, the convention of indicating non-terminal symbols in angled brackets and terminal symbols in quotes is used in the description herein. The exemplary grammar for constructing a rule is further described below.

The grammar in the example shown provides for an alarm integration algorithm that includes at least one algorithm name, one or more conditions, and one or more do statements that include one or more responses. The algorithm name, the conditions symbol and the responses symbol are all non-terminal symbols (as indicated in the grammar above by the fact that these terms are provided in angled brackets <and >) that can be satisfied by a plurality of alternatives that are provided for each of these non-terminal symbols. For the <algorithm name> symbol, the alternatives comprise a bracketed string of characters, which is a string of characters surrounded by square brackets [ ]. The <condition> symbol may be satisfied by a single condition alternative or more than one condition alternative. For the <condition> symbol, the condition symbol alternatives comprise alarm and equipment parameters and associated conditions. These condition symbol alternatives may have one or more non-terminal symbols. For example, the condition symbol alternatives in the above-described grammar have the non-terminal symbols <alarm>, <count>, <duration> and <device>. Alternatively, some of the condition alternatives may be terminal. For example, one such terminal parameter satisfying the <condition> symbol may be "power is lost." The <alarm> symbol may be satisfied by either the entry of an <alarm-type>, which is non-terminal, followed by the text "alarm" or by the entry of an <alarm-type> followed by the text "alarm from" followed by a <device>. The <alarm-type> alternatives are all terminal alternatives, which are text entries as shown in the above grammar. The <alarm-type> alternatives may indicate the type of the alarm, e.g. "LOW_RESP_RATE" would indicate a low respiratory rate alarm.

The <count> symbol is satisfied by the alternatives "1 time" or <between-2-and-100> "times." The <between-2-and-100> times symbol is satisfied by the integers "2" through "100". The <duration> symbol is satisfied by a number of non-terminal symbols including <seconds>, <minutes>, <hours>, <minutes><seconds>, <hours><minutes> or <hours><minutes><seconds>. The <hours> symbol is satisfied by either "1 hour" or <between-2-and-24> followed by "hours" where <between-2-and-24> is satisfied by the integers "2" to "24". The <minutes> symbol is satisfied by the alternatives "1 minute" or <between-2-and-59> followed by "minutes" where <between-2-and-59> is satisfied by the integers "2" to "59". The <seconds> symbol is satisfied by either "1 second" or <between-2-and-59> followed by "seconds".

The <device> symbol is satisfied by the symbol <device-manufacturer> followed by <device-model>, where both <device-manufacturer> and <device-model> are satisfied by bracketed strings.

The <responses> symbol is satisfied by either the <response> symbol or a <response> followed by a comma and the <responses> symbol, thereby enabling the <response> symbol to comprise either a single response or more than one response. The <response> symbol is satisfied by a plurality of response alternatives, which can include both terminal symbols and non-terminal symbols. As shown in the exemplary grammar, the response alternatives may include terminal symbol instructions such as an instruction to update the central monitor, an issuance of a remote notification, a decreasing of the infusion rate of a pump by a set percentage or a pausing of an infusion. Non-terminal symbols may include the response alternative of switching to <algorithm-name>, which would enable the response alternative of switching to another algorithm. As described above, the <algorithm-name> is comprised of a bracketed string of characters. Alternatively, some of the terminal responses described above could be structured as non-terminal responses. For example, the responses relating to decreasing the infusion rate could be structured as "DECREASE INFUSION RATE BY"<percentage-change>"percent" where <percentage-change> is satisfied by the integers "1" to "99".

Figure 4:
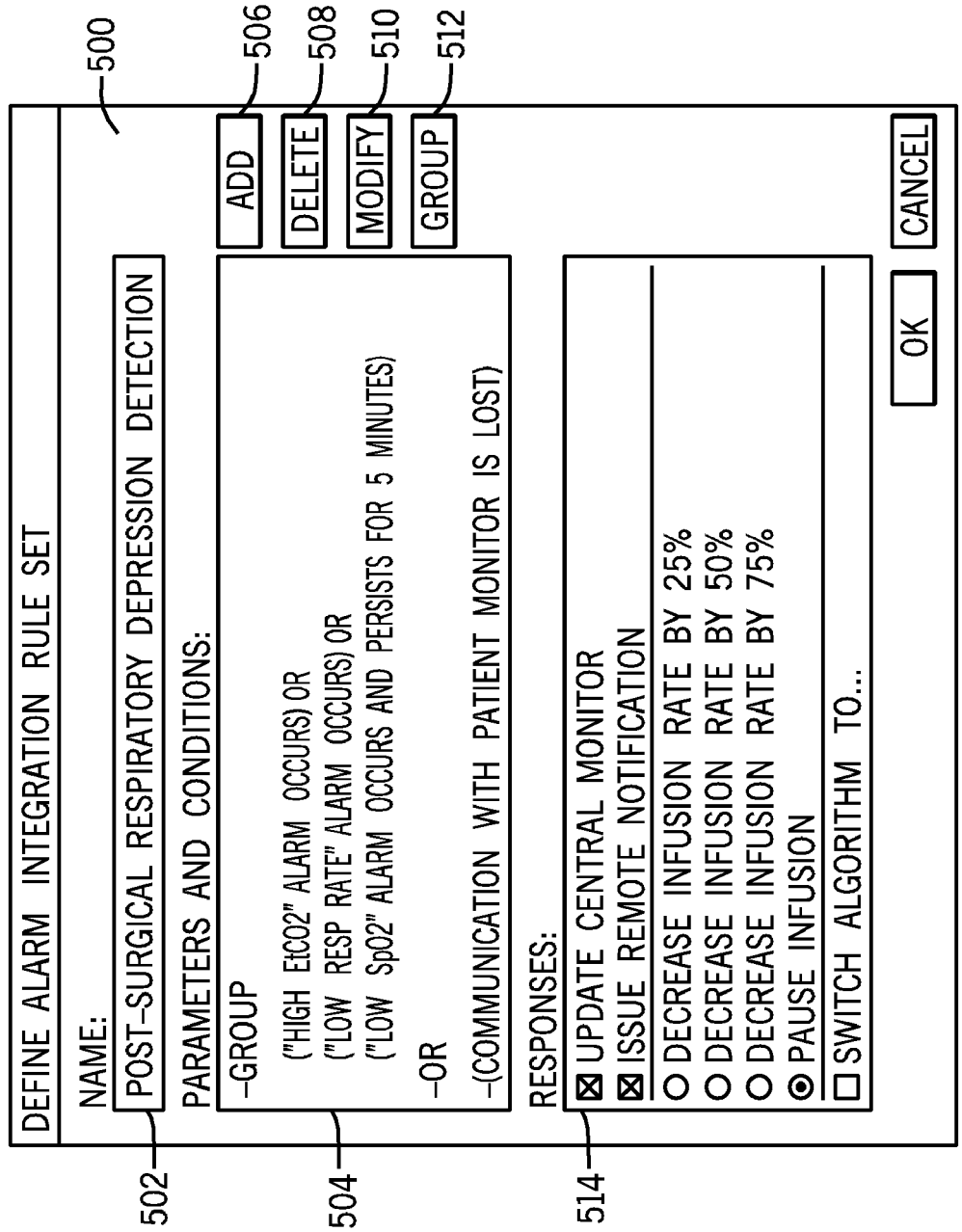
FIG. 4 is one embodiment of an exemplary interface screen display for configuring a rule set for use with a medication delivery device and patient monitoring system of the present invention.

An interface for creating rule sets is shown in FIG. 4 as 500. A first field 502, shown as the "Name" field, is provided for receiving entry of the medical delivery system rule set name. A second field 504, shown as the "Parameters" field, is provided for receiving a selection of a parameter and an associated condition, for example, "High $ETCO_2$ alarm occurs." Function buttons, 506, 508, 510, 512 are provided for receiving an input from a user to add, delete, modify or group the parameters and conditions. A third field 514, shown as the "Responses" field, is provided for receiving an authorized user's selection of the desired responses. As shown in FIG. 4, the responses may include updating a central monitor, issuing a remote notification to a caregiver, adjusting the infusion rate of a medication delivery pump, and/or switching to an alternative or different rule set.

In another aspect of the invention, once an authorized user has constructed the rule set and stored that rule set on the rule set configuration processor 140 and/or the central memory 135, the rule set may be selected by a caregiver and used to monitor the patient and patient care equipment system 100. The rule sets may be cataloged, grouped, or cross-referenced in the central storage in a variety of ways, including but not limited to by patient type (for example, an adult versus a pediatric patient), drug name (for example, morphine) or drug type (for example, opiate, narcotic, antibiotic, or cardiac), or location or ward within the care facility, which is sometimes referred to as a clinical care area (CCA), (for example, intensive care unit or ICU versus Emergency). For example, the rule sets may be organized, named, or entitled by patient parameter, e.g. "Sleep Apnea,"; patient characteristic, e.g. "Pediatric"; monitored variables; infused drugs; estimated patient drug sensitivity based upon infusion history and patient age, weight, etc.; and/or history of invalid infusion pump alarms and/or actions.

Figure 5:
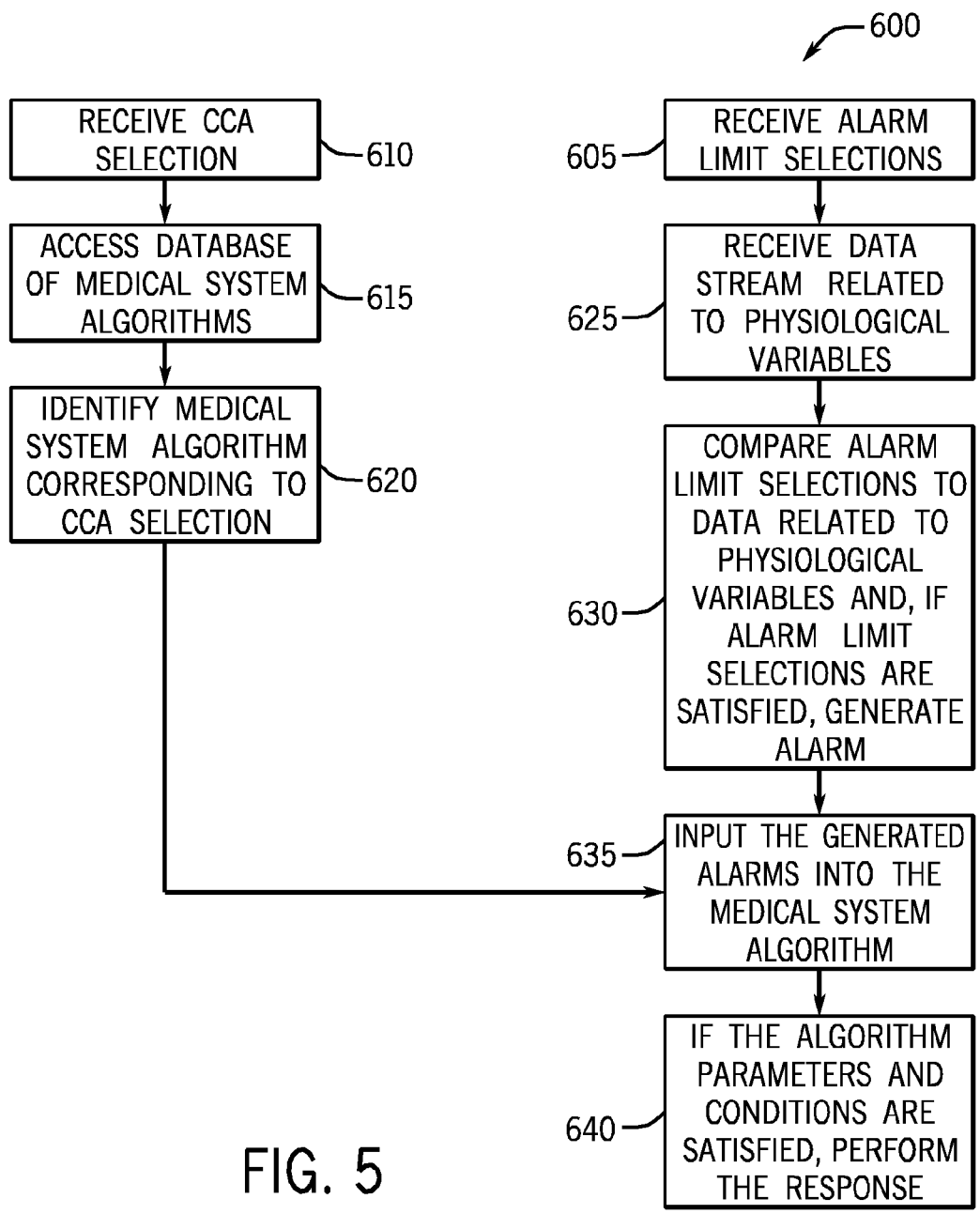
FIG. 5 is a flow chart of one embodiment of a system and method for selecting a rule set for use with a medication delivery device and patient monitoring system of the present invention.

As shown in FIG. 5, via any of the processors in the system 100 either the medical delivery pump 130 or the patient monitor 120, or both, can receive alarm limit selections input by a caregiver in step 605. As shown in step 610, the medical delivery pump input receives a particular group of rule sets, such as a particular clinical care area or all CCAs, based upon a selection input by the caregiver. In step 615, the processor 125 then accesses a database of rule sets stored on the central memory 135 that are correlated to the selection of the caregiver. In step 620, the caregiver selects the appropriate rule set; or, if only one rule set is returned, that rule set is implemented. In step 625, the patient monitor 120, and optionally the pump 130, receives the patient physiological information from the biometric sensors. The patient monitor and/or pump processor(s) compare the received physiological information, and if the alarm limits are exceeded, generate an alarm signal, which is sent to the patient monitor interface and rule set processor 125 as shown in step 630. The alarms and/or the physiological data and/or the monitored equipment data are processed according to the rule set as shown in step 635. If the rule set parameters and conditions are met, the patient monitor interface and rule set processor 125 outputs (or executes, in the case of an alternative or different rule set) the designated response or responses in step 640.

An example of a rule set configured to implement a series of new or different rule sets follows. In the case of PCA monitoring, three rule sets may be provided which respond to alarms associated with a patient's respiratory rate and $ETCO_2$ level. The first rule includes the parameter that one of the two alarms must be active for a minimum of 30 seconds prior to an action (e.g., pausing drug infusion). The second rule has a more restrictive parameter in which both alarms must be active for a minimum of 30 seconds prior to an action. The third rule defines the parameter for an infusion pause as an active $ETCO_2$ alarm for more than thirty seconds.

Although the clinician begins the PCA program using the first rule set, generation of two successive invalid pause events will lead to a change to the second rule at the time the second event is identified as invalid. This change could be automatic, in the case where the response specifies that the rule set be switched, or it could merely be suggested in the case where the rule set is configured to suggest to the caregiver that he or she switch rule sets. Similarly, if the two or more successive alarms are associated with only respiratory rate, the rule set could suggest through the pump interface that the clinician enable the third rule set. In this manner a series of rules sets are linked providing greater or lesser sensitivity to externally generated alarms. Suggestions for shifts between rule sets or changes to existing rule sets could also be generated to system administrators based on information acquired during the operation of the system.

An example of an application of a rule set in which a patient's recorded history of infusion events is used as a condition follows. To detect the potential for respiratory distress, a patient's respiratory rate and $ETCO_2$ are assessed using a respiratory monitor and a caregiver sets limits to 3-60 breaths per minute or bpm and 8-60 mmHg respectively, beyond which an alarm will be produced. With the respiratory monitor configured, the rule set is implemented within one of the processors described herein to reduce the number of false positives by requiring an alarm to be present for a minimum of 30 seconds AND within N time constants of a bolus infusion of the medication associated with respiratory distress. In this context, N is generally set to one (1) but can be modified depending upon the patient's age, disease status, co-morbidities and/or other constraints. For example, in the case of morphine delivery to a patient with liver disease, the standard time constant related to drug action is increased due to the lower metabolizing of the liver. The time constant is set to a default value associated with each drug.

Alternately, a status variable can be defined representing the patient drug load. The status variable can be used, in conjunction with individual alarms and a probability function, to improve the detection of a drug-induced adverse event and more specifically, respiratory depression. The drug load is estimated through the relationship:

Drug Load=Background Infusion+Summation (Bolus Dose* (time since dose)/(drug half-life))

Alternately, a first-order approximation for the pharmacokinetic drug elimination is:

Drug Load=Background Infusion+Summation (Bolus Dose* exp(−(time since dose)*(elimination rate constant)))

Where the elimination rate constant is estimated by the ln(2)/(half life).

In the simplest case, the function is a pre-set limit common to the particular drug. However, alternate functions can be used as well, including a percentage increase over time, a percentage increase over a pre-set limit, a sudden change in the rate of drug load, or other constraints. As a further alternative, fuzzy logic may be used to map the drug load to "high" or "low" and thereby qualify the output of the second alarm system as "probable" or "improbable". In the former situation, a rule set can be configured to create an alarm to a caregiver and to pause the delivery pump. In the latter situation, the rule set may be configured to only send an alarm to the caregiver.

In a further alternative, the drug load can be estimated as the mean drug consumption (MDC) over a period of time and used with the probability measures provided above.

In yet another example, the grammar disclosed above can be combined with both a drug infusion history for estimating the current patient drug load and the history of drug infusion requests. In particular, the demand to delivery ratio (D/D) and mean drug consumption (MDC) may be used as parameters in a rule set. A low MDC suggests alarms indicative of respiratory depression are likely invalid. However, when MDC is high, the D/D ratio is used to further qualify the drug infusion. When MDC is within 80% of maximum and D/D ratio is low (<1), the probability of a valid alarm event is likely. However, when the D/D ratio is high (>2), an indicator is provided suggesting the current pain medication is ineffective and therefore leading to high infusion rates and respiratory depression. Thus, both the calculated MDC and D/D ratio may be used in connection with respiratory rate as conditions in the rule set to provide further discrimination and decision support.

As mentioned herein, a response within a rule set can suggest or "recommend" to a caregiver to take certain actions related to the rule set and the parameters and conditions therein. For example, if a patient has not requested a PCA bolus for a twelve (12) hour period of time, the present system and method can be configured to allow an administrator or caregiver to configure a rule set to recommend to "change the therapy". Thus, the parameter that the administrator or caregiver could select would be "PCA Bolus Requests". The condition that the administrator or caregiver could select would be "None in 12 Hours". Alternative configurations could include the parameter being "No PCA Bolus Requests" and the condition being "In 12 Hours". Likewise, the response that the administrator or caregiver could select would be "Suggestion—Change Therapy [In View Of No PCA Bolus Requests In 12 Hours]". Other examples come to mind in view of the present example and description. The caregiver may either respond on their own accord or based on the system-generated suggestion respond by reduce the basal rate of infusion or wean the patient off of PCA therapy.

In another example, if a patient's pain scores are high (e.g., greater than 8 on a 10 point scale) and the patient PCA requests are frequent (e.g. more than ten (10) PCA denied events in a 4 hour period) then the present system and method can be configured to allow an administrator or caregiver to configure a rule set to recommend to "change the medication". Thus, the parameters that the administrator or caregiver could select would be "Average of Pain Scores" and "Denied PCA Bolus Requests". The Boolean operator that the administrator or caregiver could select would be an "AND" between the two parameters. The conditions the caregiver would select are "greater than 8" for the "Average Pain Scores" parameter and "More than ten (10) PCA denied events in four (4) hours" for the "Denied PCA Bolus Requests" parameter. Alternative configurations are possible. The response that the administrator or caregiver could select would be "Suggestion—Change Medication". Other examples come to mind in view of the present example and description. The caregiver may then, either on their own accord or based on the system-generated suggestion, respond by changing the medication. "Changing medication" can involve any one or a combination of the following: changing the program of the pump 130, changing to a different drug, or changing to a different drug concentration.

Any process descriptions or blocks in figures represented in the figures should be understood as representing modules, segments, or portions of code which include one or more executable instructions for implementing specific logical functions or steps in the process, and alternate implementations are included within the scope of the embodiments of the present invention in which functions may be executed out of order from that shown or discussed, including substantially concurrently or in reverse order, depending on the functionality involved, as would be understood by those having ordinary skill in the art.

Because of the interconnection of the various processors within the system 100, rule sets can be created or selected in a variety of locations within the system. By way of example and not limitation, rule sets can be created, modified, and saved at any processor in the system that has sufficient processing capability and access to memory for storage. By way of example and not limitation, rule sets can be selected on the patient monitor 120, on the pump or medication delivery device 130, on the patient monitor interface and rule set processor 125 or any combination thereof. The patient monitor interface and rule set processor 125 can be a communications engine located on the pump 130, on the patient monitor 120, on a separate module or shared between such components.

While the specific embodiments have been illustrated and described, numerous modifications come to mind without significantly departing from the invention. The scope of protection is only limited by the scope of the accompanying claims.

APPENDIX A

```
<alarm-integration-algorithm> ::=
    <algorithm-name>
    "is defined as when"
    <conditions>
    "do (" <responses> ")"
<algorithm-name> ::= <bracketed-string>
<conditions> ::=
    "(" <condition> ")" |
    "(" <conditions> ")" |
    <conditions> <boolean> <conditions>
<condition> ::=
    <alarm> "occurs" |
    <alarm> "occurs" <count> "within a period of" <duration> |
    <alarm> "occurs and is not reset or cleared within" <duration> |
    <alarm> "does not occur for at least" |
    <duration> |
```

APPENDIX A-continued

```
    "communication with" <device> "is lost" |
    "communication with" <device> "is restored"
<alarm> ::=
    <alarm-type> "alarm" |
    <alarm-type> "alarm from" <device>
<alarm-type> ::=
    "NO_BREATH" |
    "HIGH_ETCO2" |
    "LOW_ETCO2" |
    "HIGH_RESP_RATE" |
    "LOW_RESP_RATE" |
    "HI_FICO2" |
    "NO_PULSE" |
    "HIGH_PULSE_RATE" |
    "LOW_PULSE_RATE" |
    "LOW_SPO2" |
    "SPO2_SENSOR_OFF_PATIENT" |
    "SPO2_SENSOR_DISCONNECTED"
<device> ::=
    <device-manufacturer> <device-model>
<device-manufacturer> ::=
    <bracketed-string>
<device-model> ::=
    <bracketed-string>
<responses> ::=
    <response> |
    <response> "," <responses>
<response> ::=
    "UPDATE_CENTRAL_MONITOR" |
    "ISSUE REMOTE_NOTIFICATION" |
    "DECREASE_INFUSION_RATE_BY_25%" |
    "DECREASE_INFUSION_RATE_BY_50%" |
    "DECREASE_INFUSIONCRATE_BY_75%" |
    "PAUSE_INFUSION" |
    "SWITCH_ALGORITHM_TO" <algorithm-name>
<boolean> ::=
    "and" | "or"
<bracketed-string> ::=
    "[" <string> "]"
<string> ::=
    <char> |
    <char> <string>
<char> ::=
    <letter> |
    <digit> |
    <space>
<letter> ::=
    "a" | "b" | ... | "z" |
    "A" | "B" | ... | "Z"
<digit> ::=
    "0" | "1" | ... | "9"
<space> ::=
    " "
<count> ::=
    "1 time" |
    <between-2-and-100> "times"
<duration> ::=
    <hours> <minutes> <seconds> |
    <hours> <minutes> |
    <hours> <seconds> |
    <minutes> <seconds> |
    <hours> |
    <minutes> |
    <seconds>
<hours> ::=
    "1 hour" |
    <between-2-and-24> "hours"
<minutes> ::=
    "1 minute" |
    <between-2-and-59> "minutes"
<seconds> ::=
    "1 second" |
    <between-2-and-59> "seconds"
<between-2-and-100> ::= "2" | "3" | ... | "100"
<between-2-and-59> ::= "2" | "3" | ... | "59"
```

One exemplary simple rule according to the grammar is listed below.

```
[Simple rule set]
    is defined as when
        (HIGH_ETCO2 alarm occurs)
    do
        (PAUSE_INFUSION)
```

Another such more complicated exemplary rule set that has several parameters as well as several responses according to the grammar listed below.

```
[More complicated rule set with multiple responses]
    is defined as when
        (
            (
                (HIGH_ETCO2 alarm occurs) or
                (LOW_RESP_RATE alarm occurs) or
                (LOW_SPO2 alarm occurs and is not reset or cleared
                    within 5 minutes)
            )
            or
            (communication with patient monitor is lost)
        )
    do
        (
            PAUSE_INFUSION,
            ISSUE_REMOTE_NOTIFICATION,
            UPDATE_CENTRAL_MONITOR
        )
```

What is claimed is:

1. A method for implementing a medical system algorithm by an authorized medical caregiver, the steps of the method comprising:

providing a context free grammar to define the medical system algorithm, the grammar comprising non-terminal parameter symbols and terminal parameter symbols that are configured to be satisfied by a plurality of non-terminal medical system parameters and terminal medical system parameters, respectively, the grammar further comprising non-terminal condition symbols and terminal condition symbols that are configured to be satisfied by a plurality of non-terminal medical system conditions and terminal medical system conditions, respectively, the grammar further comprising a response symbol that is configured to be satisfied by a plurality of medical system responses;

receiving a first parameter selection comprising at least of one of the non-terminal parameters or at least one of the terminal parameters, defined by the grammar;

receiving a respective first medical system condition selection corresponding to the at least one of the non-terminal parameter symbol or terminal parameter symbol for the selected first parameter selection defined by the grammar;

receiving a medical system response selection;

generating the medical system algorithm from the first parameter selection, the first medical system condition selection, and the medical system response selection; and storing the generated medical system algorithm for later use by an automated medical device wherein the generated medical system algorithm can be selected independently from other stored medical system algorithms.

2. The method of claim 1 wherein the first parameter selection comprises at least one of the non-terminal parameter symbols and at least one of the terminal parameter symbols defined by the grammar.

3. The method of claim 1 wherein the response symbol comprises one of a non-terminal response symbol and a terminal response symbol, wherein the response symbol is configured to be satisfied by non-terminal medical system responses and terminal medical system responses, respectively.

4. The method of claim 1 wherein the step of receiving a medical system response comprises receiving a non-terminal medical system response.

5. The method of claim 1 further comprising the steps of: receiving a second parameter selection comprising at least of one of the non-terminal parameter symbols or at least one of the terminal parameter symbols defined by the grammar; and, receiving a respective second medical system condition selection corresponding to the at least one of the non-terminal parameter symbol or terminal parameter symbol for the selected second parameter selection defined by the grammar.

6. The method of claim 5 wherein the second parameter selection comprises at least one of the non-terminal parameter symbols and at least one of the terminal parameter symbols defined by the grammar.

7. The method of claim 5 wherein the first medical system parameter selection is a first alarm selection and wherein the second medical system parameter selection is a second alarm selection, different than the first alarm selection.

8. The method of claim 7 wherein the first alarm selection is for an alarm related to a medical pump function and wherein the second alarm selection is for an alarm related to a patient monitor function.

9. The method of claim 8 wherein the alarm related to the medical pump function is one of a loss of communication with the medical pump alarm and status of medical pump parameter alarm.

10. The method of claim 8 wherein the alarm related to the patient monitor function is one of a loss of communication with the patient monitor alarm and status of a patient monitor parameter alarm.

11. The method of claim 1 wherein the first medical system parameter selection is a first alarm selection.

12. The method of claim 11 wherein the first alarm selection is one of an alarm related to a medical pump function and wherein the second alarm selection is for an alarm related to a patient monitor function.

13. The method of claim 1 wherein the first medical system parameter is a component of a medical system condition.

14. The method of claim 1 further comprising the step of: receiving a first Boolean connector selection, wherein the step of generating the medical system algorithm is further generated from the first Boolean connector.

15. The method of claim 14 further comprising the step of: receiving a second Boolean connector selection, wherein the step of generating the medical system algorithm is further generated from the second Boolean connector.

16. The method of claim 1 wherein the medical system parameters are alternative medical system parameters within the grammar, wherein the alternative medical parameters do not represent a medical state or condition of a patient.

17. The method of claim 1 wherein at least one of the medical system parameters defined by the grammar comprises both terminal and non-terminal components.

18. The method of claim 1 wherein the step of receiving a response selection comprises receiving a plurality of response selections.

19. The method of claim 1 wherein the first medical system parameter selection is received through a first region of a user interface display and wherein the medical system response selection is received through a second region of the user interface display.

20. The method of claim 16 wherein at least one of the alternative medical system parameters defined by the grammar comprises a change in communication state with a medical device.

21. The method of claim 1 wherein the first condition selection comprises at least one of a time symbol, a patient drug load symbol, a delivery to demand load symbol, a mean drug consumption symbol, and a patient drug factor symbol.

22. The method of claim 1 wherein the medical system response comprises at least one of an implementation of another medical system algorithm, an adjustment of a drug delivery rate, a pause to a drug delivery, and a medical diagnosis.

23. The method of claim 1 further comprising the steps of: receiving a clinical care area (CCA) selection for the medical system algorithm for categorizing the medical system algorithm by CCA; and, associating the CCA selection with the medical system algorithm and storing the association.

* * * * *